US00PP29023P2

(12) United States Plant Patent
Chen

(10) Patent No.: US PP29,023 P2
(45) Date of Patent: Feb. 27, 2018

(54) ***ANTHURIUM* PLANT NAMED 'RYN2011113'**

(50) Latin Name: *Anthurium andreanum*
Varietal Denomination: RYN2011113

(71) Applicant: DUMMEN GROUP B.V., De Lier (NL)

(72) Inventor: Meng Chen, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/530,036

(22) Filed: Nov. 22, 2016

(51) Int. Cl.
*A01H 5/02* (2006.01)

(52) U.S. Cl.
USPC ..... Plt./369

(58) Field of Classification Search
USPC ..... Plt./369
See application file for complete search history.

*Primary Examiner* — Annette H Para
(74) *Attorney, Agent, or Firm* — C. A. Whealy

(57) ABSTRACT

A new and distinct cultivar of *Anthurium* plant named 'RYN2011113', characterized by its compact, upright, outwardly arching and uniform plant habit; freely clumping growth habit; bushy and dense plants; glossy dark green-colored leaves; early and freely flowering habit; large rounded fire red-colored spathes that are positioned at the foliar plane of the plant on strong and erect scapes; and good inflorescence longevity.

1 Drawing Sheet

Botanical designation: *Anthurium andreanum.*
Cultivar denomination: 'RYN2011113'.

BACKGROUND OF THE INVENTION

The present invention relates to a new and distinct cultivar of *Anthurium* plant, botanically known as *Anthurium andreanum* and hereinafter referred to by the name 'RYN2011113'.

The new *Anthurium* plant is a product of a controlled breeding program conducted by the Inventor in De Lier, The Netherlands. The objective of the breeding program is to create new compact *Anthurium* plants that flower early and have large attractive inflorescences.

The new *Anthurium* plant originated from a cross-pollination made by the Inventor in mid-August, 2009 in De Lier, The Netherlands of a proprietary selection of *Anthurium andreanum* identified as code number AT06-000087-001, not patented, as the female, or seed, parent with a proprietary selection of *Anthurium andreanum* identified as code number AT06-000068-001, not patented, as the male, or pollen, parent. The new *Anthurium* was discovered and selected by the Inventor as a single flowering plant within the progeny of the stated cross-pollination in a controlled greenhouse environment in De Lier, The Netherlands in late September, 2010.

Asexual reproduction of the new *Anthurium* plant by tissue culture in a controlled environment in Lochristi, Belgium since mid-February, 2011 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'RYN2011113'. These characteristics in combination distinguish 'RYN2011113' as a new and distinct *Anthurium* plant:

1. Compact, upright, outwardly arching and uniform plant habit.
2. Freely clumping growth habit; bushy and dense plants.
3. Glossy dark green-colored leaves.
4. Early and freely flowering habit.
5. Large rounded fire red-colored spathes that are positioned at the foliar plane of the plant on strong and erect scapes.
6. Good inflorescence longevity.

Plants of the new *Anthurium* differ from plants of the female parent selection in the following characteristics:

1. Plants of the new *Anthurium* are more compact than plants of the female parent selection.
2. Plants of the new *Anthurium* are bushier and denser than plants of the female parent selection.
3. Plants of the new *Anthurium* have smaller spathes than plants of the female parent selection.

Plants of the new *Anthurium* differ from plants of the male parent selection in the following characteristics:

1. Plants of the new *Anthurium* have larger spathes than plants of the male parent selection.
2. Plants of the new *Anthurium* and the male parent selection differ in spathe color as plants of the male parent selection have orange-colored spathes.

Plants of the new *Anthurium* can also be compared to plants of *Anthurium andreanum* 'RYN2009006', not patented. In side-by-side comparisons, plants of the new *Anthurium* differ from plants of 'RYN2009006' in the following characteristics:

1. Plants of the new *Anthurium* are slightly larger than plants of 'RYN2009006'.

2. Plants of the new *Anthurium* and 'RYN2009006' differ slightly in leaf color.
3. Plants of the new *Anthurium* have inflorescences with single spathes whereas plants of 'RYN2009006' have double spathes.

BRIEF DESCRIPTION OF THE PHOTOGRAPH

The accompanying photograph illustrates the overall appearance of the new *Anthurium*. The photograph shows the colors as true as it is reasonably possible to obtain in colored reproductions of this type. Colors in the photograph may differ slightly from the color values cited in the detailed botanical description which accurately describe the colors of the new *Anthurium*.

The photograph is a side perspective view of a typical plant of 'RYN2011113' grown in a container.

DETAILED BOTANICAL DESCRIPTION

The aforementioned photograph and following observations and measurements describe plants grown in 14-cm containers in De Lier, The Netherlands during the late summer in a glass-covered greenhouse. Plants were grown under conditions and practices which approximate those generally used in commercial *Anthurium* production. During the production of the plants, day temperatures ranged from about 22° C. to 25° C., night temperatures ranged from about 17° C. to 20° C. and light levels ranged from 1.6 to 2 klux. Plants were 30 weeks old when the photographs and the detailed description were taken. In the following description, color references are made to The Royal Horticultural Society Colour Chart, 2001 Edition, except where general terms of ordinary dictionary significance are used.

Botanical classification: *Anthurium andreanum* 'RYN2011113'.

Parentage:

*Female, or seed, parent*.—Proprietary selection of *Anthurium andreanum* identified as code number AT06-000087-001, not patented.

*Male, or pollen, parent*.—Proprietary selection of *Anthurium andreanum* identified as code number AT06-000068-001, not patented.

Propagation:

*Type*.—By tissue culture.

*Time to initiate roots, summer*.—About two weeks at temperatures about 20° C.

*Time to initiate roots, winter*.—About three weeks at temperatures about 15° C.

*Time to produce a rooted young plant, summer*.—About 70 days at temperatures about 20° C.

*Time to produce a rooted young plant, winter*.—About 91 days at temperatures about 15° C.

*Root description*.—Medium in thickness, fleshy; typically pinkish in color, actual color of the roots is dependent on substrate composition, water quality, fertilizer type and formulation, substrate temperature and physiological age of roots.

*Rooting habit*.—Freely branching, medium density.

Plant description:

*Plant shape*.—Compact, upright and outwardly spreading plant habit; broad inverted triangle; symmetrical.

*Growth habit*.—Freely clumping, bushy and dense; vigorous growth habit.

*Plant height, from soil level to top of leaf plane*.—About 40 cm.

*Plant height, from soil level to top of inflorescences*.—About 40 cm.

*Plant diameter or spread*.—About 60 cm.

Leaf description:

*Arrangement*.—Alternate; simple.

*Length*.—About 20 cm.

*Width*.—About 12 cm.

*Shape*.—Cordate.

*Apex*.—Apiculate.

*Base*.—Auriculate.

*Margin*.—Entire.

*Texture and luster, upper and lower surfaces*.—Smooth, glabrous; leathery; glossy.

*Venation pattern*.—Pinnate.

*Color*.—Developing leaves, upper surface: Close to 147A. Developing leaves, lower surface: Close to 197A. Fully expanded leaves, upper surface: Close to 139A; venation, close to 137B. Fully expanded leaves, lower surface: Close to 137C; venation, close to 137B.

*Petioles*.—Length: About 25 cm. Diameter, just below geniculum: About 3 mm. Diameter, at plant base: About 3 mm. Strength: Moderately strong. Texture and luster, upper and lower surfaces: Smooth, glabrous; moderately glossy. Color, upper and lower surfaces: Close to 148A. Geniculum length: About 2 cm. Geniculum diameter: About 5 mm. Geniculum texture and luster: Smooth, glabrous; moderately glossy. Geniculum color, upper and lower surfaces: Close to 143C.

Inflorescence description:

*Inflorescence arrangement and flowering habit*.—Spathes with spadices that are positioned at the foliar plane on strong and erect scapes; flowering structures arise from leaf axils; freely and continuous flowering year-round in The Netherlands; typically about seven open inflorescences per plant at one time.

*Fragrance*.—None detected.

*Inflorescence longevity*.—Inflorescences last about six to twelve weeks on the plant; inflorescences last about 20 days as a cut flower; inflorescences persistent.

*Spathes*.—Length: About 9 cm. Width: About 10 cm. Shape: Cordate. Apex: Cuspidate. Base: Cordate. Margin: Entire. Texture and luster, upper and lower surfaces: Smooth, glabrous; leathery; glossy. Color: When developing and fully developed, front surface: Close to 45A; color does not fade with development. When developing and fully developed, rear surface: Close to 45B; color does not change with development.

*Spadix*.—Length: About 4.5 cm. Diameter: About 6 mm. Shape: Columnar, tapering towards the apex; apex, obtuse; base, obtuse; cross-section, rounded. Aspect: Mostly erect. Color: Immature: Close to 17A. Mature: Close to 144B. Flowers: Quantity per spadix: Numerous, about 400. Shape: Rounded. Height: About 1 mm. Diameter: About 1 mm. Color, immature: Close to 17A. Color, mature: Close to 144B. Pollen amount: Scarce. Pollen color: Close to 158B. Stigma shape: Ovoid. Stigma color: Close to 155D. Ovary color: Close to 155D.

*Scape*.—Length: About 35 cm. Diameter: About 3 mm. Strength: Moderately strong. Aspect: Erect to slightly outwardly slanted. Color: Close to 148A.

*Seed and fruit*.—Seed and fruit development has not been observed on plants of the new *Anthurium*.

Pathogen & pest resistance: Plants of the new *Anthurium* have not been observed to be resistant to pathogens or pests common to *Anthurium* plants.

Temperature tolerance: Plants of the new *Anthurium* have been observed to be tolerant to temperatures ranging from about 15° C. to about 35° C.

It is claimed:

1. A new and distinct *Anthurium* plant named 'RYN2011113' as illustrated and described.

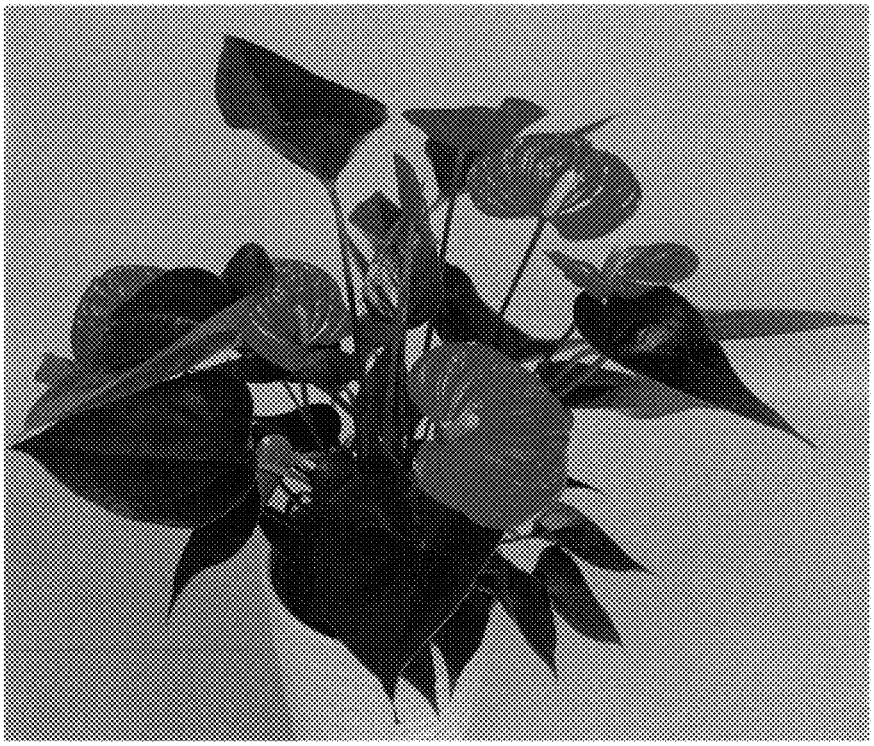

* * * * *